(12) United States Patent
Brito De La Fuente et al.

(10) Patent No.: US 10,342,775 B2
(45) Date of Patent: Jul. 9, 2019

(54) VITAMIN A FOR PARENTERAL ADMINISTRATION

(71) Applicant: FRESENIUS KABI DEUTSCHLAND GMBH, Bad Homburg (DE)

(72) Inventors: Edmundo Brito De La Fuente, Friedrichsdorf (DE); Crispulo Gallegos-Montes, Bad Homburg (DE); Lida A. Quinchia-Bustamente, Bad Homburg (DE); Telli Hekmatara, Frankfurt am Main (DE); Michael Betz, Memmingen (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/575,984

(22) PCT Filed: May 20, 2016

(86) PCT No.: PCT/EP2016/061356
§ 371 (c)(1),
(2) Date: Nov. 21, 2017

(87) PCT Pub. No.: WO2016/188874
PCT Pub. Date: Dec. 1, 2016

(65) Prior Publication Data
US 2018/0147174 A1 May 31, 2018

(30) Foreign Application Priority Data

May 22, 2015 (EP) .................................... 15168943

(51) Int. Cl.
| | | |
|---|---|---|
| *A61K 9/00* | (2006.01) |
| *A61P 3/02* | (2006.01) |
| *A61K 31/07* | (2006.01) |
| *A61K 47/02* | (2006.01) |
| *A61K 47/10* | (2017.01) |
| *A61K 47/12* | (2006.01) |
| *A61K 47/24* | (2006.01) |
| *A61K 47/34* | (2017.01) |
| *A61K 47/44* | (2017.01) |
| *A61K 9/107* | (2006.01) |
| *A61K 31/215* | (2006.01) |

(52) U.S. Cl.
CPC .......... *A61K 31/215* (2013.01); *A61K 9/0019* (2013.01); *A61K 9/1075* (2013.01); *A61K 31/07* (2013.01); *A61K 47/02* (2013.01); *A61K 47/10* (2013.01); *A61K 47/12* (2013.01); *A61K 47/24* (2013.01); *A61K 47/34* (2013.01); *A61K 47/44* (2013.01); *A61P 3/02* (2018.01)

(58) Field of Classification Search
CPC ...... A61K 31/07; A61K 31/215; A61K 47/02; A61K 47/10; A61K 47/12; A61K 47/24; A61K 47/34; A61K 47/44; A61K 9/0019; A61K 9/1075; A61P 3/02
See application file for complete search history.

(56) References Cited

U.S. PATENT DOCUMENTS 5,188,817 A * 2/1993 Ozick .................... A61K 8/671
424/435
5,925,684 A * 7/1999 Schweikert .......... A61K 9/1075
424/400

OTHER PUBLICATIONS

Tomsits et al., Journal of Pediatric Gastroenterology and Nutrition: Oct. 2010—vol. 51—Issue 4—pp. 514-521. (Year: 2010).*

* cited by examiner

*Primary Examiner* — Aradhana Sasan
(74) *Attorney, Agent, or Firm* — Hylton-Rodic Law PLLC

(57) ABSTRACT

The present disclosure relates to emulsions for parenteral administration comprising 1000 to 5000, preferably 1500 to 3000 IU, vitamin A per ml, wherein the emulsions are free of polysorbates and polyoxyethylene/polyoxypropylene block copolymers. The present disclosure further relates to a method for manufacturing the compositions of the disclosure as well as to the use of the compositions of the disclosure.

20 Claims, No Drawings

VITAMIN A FOR PARENTERAL ADMINISTRATION

CROSS REFERENCE TO RELATED APPLICATIONS

This application is the national phase under 35 USC 371 of international application no. PCT/EP2016/061356, filed May 20, 2016, which claims the benefit of the priority date of European application no. 15168943.7, filed May 22, 2015. The contents of the aforementioned applications are incorporated herein in their entireties.

FIELD OF THE DISCLOSURE

The present disclosure relates to pharmaceutical compositions for parenteral administration comprising vitamin A.

The present disclosure further relates to a method for manufacturing the compositions of the disclosure as well as to the use of the compositions of the disclosure.

BACKGROUND

Being necessary for orderly growth and differentiation of tissues, vitamin A is one of the most important micronutrients affecting the health of children. In the developing world, vitamin A supplementation programmes significantly reduce infant mortality as well as the incidence of xerophthalmia, respiratory infection, and morbidity from gastrointestinal disease. Supplementing newborn infants with vitamin A within 48 hours of birth reduces infant mortality by almost a quarter, with the greatest benefit to those of low birth weight. In the developed world, most infants and children are vitamin A sufficient. Term infants are well supplied with vitamin A in utero, and both human milk and infant formulae contain adequate amounts of vitamin A for normal growth and health. Unfortunately, vitamin A sufficiency cannot be assumed for preterm infants. Born with inadequate body stores of vitamin A and often unable to tolerate routine oral supplementation, they are prone to diseases of the eye and respiratory and gastrointestinal tract (Mactier and Weaver, Arch Dis Child Fetal Neonatal Ed 2005; 90: F103-F108).

Due to their immature gastrointestinal tract, many low birth weight and almost all extremely low birth weight infants cannot absorb and digest enteral nutrition in the first days after birth.

Thus, parenteral administration is the only suitable route for supplementing these infants with vitamin A.

Presently, the recommended doses for parenterally administered vitamin A vary between 700 and 1700 International Units per kg per day.

In order to warrant flexible, individual and independent vitamin A dosing, vitamin A should advantageously be available as a mono vitamin product rather than being fixed part of a pre-mixed multivitamin preparation.

To our knowledge, there is only one such vitamin A product commercially available for parenteral supplementation of vitamin A: Aquasol A™ (Hospira). The product is an aqueous solution of vitamin A and comprises 15 mg retinol (50000 IU, as retinol palmitate) per ml of the composition. Further ingredients are chlorobutanol (as a preservative) and polysorbate (as a solubilizer; retinol palmitate is practically insoluble in water). Aquasol A™ is approved for intramuscular application.

Intramuscular injection, however, is extremely painful, especially to newborn infants, and may cause infections, tissue irritations, muscle damage, haematomas and nerve lesions. More severely, polysorbates have been associated with the E-Ferol syndrome (thrombocytopenia, renal dysfunction, hepatomegaly, cholestasis, ascites, hypotension and metabolic acidosis) in low birthweight infants.

U.S. Pat. No. 5,925,684 relates to emulsions for parenteral administration comprising at least one carotenoid in a concentration of 0.1 to 10 wt. %. These emulsions are stabilized by means of Poloxamer 188.

Carotenoids have the tendency to stick to plastic surfaces and are thus not ideal vitamin A derivatives for the preparation of storage stable vitamin A compositions.

Poloxamers are synthetic polyoxyethylene/polyoxypropylene block copolymers that may cause allergy and/or intolerance.

Thus there is a need for compositions overcoming the drawbacks described above, i.e. there is a need for safe, compatible and stable compositions suitable for the parenteral supplementation of vitamin A, specifically for compositions that may readily be administered intravenously and be mixed with customary parenteral nutrition products.

SUMMARY

It has been found that the above mentioned difficulties and drawbacks may be overcome by providing vitamin A in form of an emulsion for parenteral administration. The emulsions according to the present disclosure are stable, even in the absence of polysorbate and polyoxyethylene/polyoxypropylene block copolymers, safe and compatible. Moreover, they may readily be administered intravenously and mixed with customary parenteral nutrition products.

In particular, the present disclosure relates to emulsions for parenteral administration comprising 1000 to 5000, preferably 1500 to 3000 IU, vitamin A per ml, being free of polysorbate and poloxamer (polyoxyethylene/polyoxypropylene block copolymers).

Particularly preferred embodiments are set forth in the claims.

DETAILED DESCRIPTION

Vitamin A

The term "vitamin A" refers to a group of unsaturated nutritional organic compounds including retinol, retinal, retinoic acid, and several pro-vitamin A carotenoids, among which beta-carotene is the most important.

In foods of animal origin, the major form of vitamin A is an ester of retinol, primarily retinyl palmitate, which is converted to retinol in the small intestine. The retinol form functions as storage form of the vitamin, and can be converted into its visually active aldehyde form, retinal.

The amount of vitamin A is specified in international units (IU). 1 IU vitamin A is equal to 0.3 µg retinol and 1.8 µg β-carotene.

Vitamin A amounts may also be specified in retinol equivalents (RE). One RE corresponds to 1 µg retinol and 6 µg β-carotene (dissolved in oil).

Preferably, the compositions according to the present disclosure comprise vitamin A in a form other than that of beta-carotene, more preferably in a form other than carotenoid.

Most preferably, the compositions according to the present disclosure comprise vitamin A in form of retinyl palmitate.

Preferably, vitamin A is the sole vitamin comprised as an active ingredient, i.e. preferably the compositions according to the present disclosure are mono vitamin preparations.

Emulsion

The compositions according to the present disclosure are emulsions, preferably oil-in-water emulsions, i.e. the continuous phase is aqueous and comprises oil droplets. The emulsion comprises the continuous aqueous phase and preferably 2 wt. % to 30 wt. % of an oil phase based on the total weight of the emulsion. More preferably, the emulsion comprises 5 wt % to 30 wt. % of an oil phase based on the total weight of the emulsion, even more preferably 5 wt. % to 25 wt. % based on the total weight of the emulsion, most preferably 10 wt. % to 20 wt. % based on the total weight of the emulsion. For example, the emulsion comprises 10 wt. % or 20 wt. % of an oil phase based on the total weight of the emulsion.

The aqueous phase comprises water in purity suitable for parenteral administration, i.e. water for injection.

Oil-in-water emulsions for parenteral administration have to be sterile, pyrogen-free, well tolerated, isotonic or as close as possible to isotonicity, free of particulate impurities and storage stable. Their pH should be as close as possible to the pH of the blood.

Because fat globules larger than 5 µm may induce occlusion of the microvasculature, oil-in-water emulsions for parenteral administration must contain only very few oil droplets larger than 5 µm.

The USP refers to this parameter as "$PFAT_5$", which should not exceed 0.05 (compare USP 36 NF31 <729>).

Scientifically correct, the $PFAT_5$ value refers to the volume-weighted, large-diameter fat globule limits of the dispersed phase, expressed as the percentage of fat residing in globules larger than 5 µm ($PFAT_5$).

The Oil Phase

The oil phase may comprise a variety of different lipids, e.g. oils, e.g. soybean oil, olive oil, fish oil, fish oil extract, safflower oil, corn oil, sunflower oil, coconut oil, palm kernel oil, rapeseed oil, medium chain triglycerides (MCT) and mixtures thereof.

Preferably, the oil phase comprises one or more oils selected from the group consisting of soybean oil, olive oil, fish oil, fish oil extract and MCT. More preferably, the oil phase comprises soybean oil, olive oil, fish oil and MCT.

The term "fish oil" refers to "purified fish oil" and to "purified fish oil rich in omega 3 fatty acids", the latter according to the European Pharmacopoeia 6.0 comprising at least 9 wt. % of the omega-3-fatty acid docosahexaenoic acid (DHA) and at least 13 wt. % of the omega-3 fatty acid eisosapentaenoic acid (EPA) expressed as triglycerides.

The term "fish oil extract" refers to mixtures highly concentrated in EPA and DHA obtained e.g. from fish oil e.g. by supercritical fluid extraction and subsequent purification via e.g. chromatographic methods. Alternatively, the oil can be extracted using extraction techniques such as the one described in U.S. Pat. No. 6,750,048. Additional extraction and/or purification techniques are described in WO2001/076715 and WO2001/076385. The sum of EPA and DHA contained in these fish oil extracts is at least 500 milligram per gram of extract.

The fish oil extract comprises EPA and DHA in esterified form, e.g. in form of triglycerides or ethyl esters.

The term "medium chain triglycerides" refers to triglycerides of fatty acid being 6 to 12 carbon atoms in length, including caproic acid, caprylic acid, capric acid and lauric acid.

The Emulsifier

The emulsions according to the present disclosure comprise at least one pharmaceutically acceptable emulsifier. The term "emulsifier" refers to compounds which stabilize the composition by reducing the interfacial tension between the oil phase and the water phase and which typically comprise at least one hydrophobic group and at least one hydrophilic group. These emulsifiers (which may also be referred to as surfactants) are preferably used in amounts effective to provide, optionally together with further surfactants present, a stable and even distribution of the oil phase within the aqueous phase. In particular, the emulsifier is selected from the group of emulsifiers that have been approved for parenteral administration.

Preferably, the at least one emulsifier is lecithin. Within the meaning of the present disclosure the term "lecithin" refers to naturally occurring or synthetic lecithin that may be suitably refined. Suitable lecithins include, but are not limited to, lecithins derived from egg, corn or soybean or mixtures thereof. Lecithins are typically mixtures of diglycerides of fatty acids linked to the choline ester of phosphoric acid and can contain differing amounts of other compounds depending on the method of isolation. Typically, commercial lecithin is a mixture of acetone-insoluble phosphatides. Preferably, the lecithin is obtained from egg or from seeds including soybean and corn, using methods well known in the art. Lecithin obtained from soybean is referred to herein as soy lecithin. Lecithin obtained from egg is referred to herein as egg lecithin.

Preferably, the emulsions comprise lecithin as emulsifier, more preferably the lecithin is selected from the group consisting of egg lecithin, soy lecithin, and mixtures thereof. These are commercially available, e.g. under the trade names Epikurin™ 170 (soy lecithin), PL 90 or Lipoid E80 (both egg lecithin).

Preferably, the lecithin is used in an amount of 0.5 to 5 wt. %, more preferably 0.5 to 3 wt. %, most preferably 1.0 to 2.5 wt. %.

Alternatively, krill oil may be used as an emulsifier. Krill oil is an extract prepared from a species of antarctic krill, *Euphausia superba*. It has obtained GRAS (generally recognized as safe) status from the FDA and is commercially available, e.g. from Olympic Seafood (Bioriginal Europe/Asia B.V.) and Aker BioMarine Antarctic AS. The emulsifying properties of krill oil mainly rely on its content in phospholipids (including phosphatidylcholine, phosphatidylethanolamine and phosphatidylinositol).

The Antioxidant

The emulsion may comprise at least one pharmaceutically acceptable antioxidant.

An antioxidant useful in the emulsion of the disclosure may be any pharmaceutically acceptable compound having antioxidant activity, for example, the antioxidant may be selected form the group consisting of sodium metasulfite, sodium bisulfite, sodium sulfite, sodium thiosulfate, thioglycerol, thiosorbitol, thioglycolic acid, cysteine hydrochloride, n-acetyl-cysteine, citric acid, alpha-tocopherol, beta-tocopherol, gamma-tocopherol, soluble forms of vitamin E, butylated hydroxyanisole (BHA), butylated hydroxytoluene (BHT), t-butylhydroquinone (TBHQ), monothioglycerol, propyl gallate, histidine, enzymes such as superoxide dismutase, catalase, selenium glutathione peroxidase, phospholipid hydroperoxide and glutathione peroxidase, Coenzyme Q10, tocotrienols, carotenoids, quinones, bioflavonoids, polyphenols, bilirubin, ascorbic acid, isoascorbic acid, uric acid, metal-binding proteins, ascorbic acid palmitate, an antioxidant obtained or obtainable from rosemary, rosemary extract and mixtures thereof.

The at least one antioxidant is in particular selected from the group consisting of alpha-tocopherol, beta-tocopherol, gamma-tocopherol, ascorbic acid, and mixtures of two or more thereof.

If present, the total amount of agents with antioxidant activity is preferably in the range of from 0.01 wt. % to 0.05 wt %, more preferably from 0.01 wt. % to 0.04 wt. %, more preferably from 0.01 wt. % to 0.03 wt. %, and even more preferably from 0.015 wt. % to 0.025 wt. % based on the total weight of the emulsion.

The Tonicity Agent

The emulsion may comprise at least one pharmaceutically acceptable tonicity agent. Tonicity agents are used to confer tonicity. Suitable tonicity agents may be selected from the group consisting of sodium chloride, mannitol, lactose, dextrose, sorbitol and glycerol.

Preferably, the tonicity agent is glycerol.

Preferably, the total amount of tonicity agents is in the range of 0.1 to 10 wt. %, more preferably from 1 wt. % to 5 wt. %, more preferably from 1 wt. % to 4 wt. %, more preferably 1 wt. % to 3 wt. %, more preferably from 1.5 wt. % to 2.8 wt. %, and even more preferably from 2.0 wt. % to 2.8 wt. % based on the total weight of the emulsion.

In case the tonicity agent is glycerol the most preferred amount is 2.0 wt. % to 2.5 wt. % based on the total weight of the emulsion.

Preferably, the emulsion has an osmolality in the range of 305 to 420 mOsmol/kg, measured with a Vapor Pressure Osmometer, Model 5520 (Vapro™) according to USP <785>.

pH Adjustment

The pH of the emulsion may be adjusted by adding solutions of conventionally known acids or bases such as HCl and NaOH or through the use of buffers, such as phosphate buffers.

The final pH of the emulsion is preferably in the range of from 6 to 9, more preferably between 7.5 and 9.

Preferably, the pH of the emulsion according to the disclosure is adjusted using a solution of NaOH.

The Co-Surfactant

The emulsion according to the disclosure may further comprise a pharmaceutically acceptable co-surfactant.

A co-surfactant is an amphiphilic molecule, i.e. a molecule that contains both hydrophilic and lipophilic groups. Usually, a co-surfactant substantially accumulates with the emulsifier at the interfacial layer. The hydrophile-lipophile balance (HLB) number is used as a measure of the ratio of hydrophilic and lipophilic groups present in a surfactant or co-surfactant, respectively. Usually, a co-surfactant with a very low HLB value (thus with a relatively high affinity to oil) is used together with a surfactant with a high HLB to modify the overall HLB of the system. Unlike the emulsifier, the co-surfactant may not be capable of forming self-associated structures, like micelles, on its own. Several kinds of molecules including nonionic emulsifiers, alcohols, amines and acids, can function as co-surfactants in a given system. The co-surfactant is usually used in a lower amount than that of the emulsifier. Apart from modifying the overall HLB value of the system, the co-surfactant has the effect of further reducing the interfacial tension and increasing the fluidity of the interface. Co-surfactants may also adjust the curvature of the interfacial film by partitioning between the tails of the emulsifier chains, allowing greater penetration of the oil between the emulsifier tails.

Preferably, the co-surfactant is a free unsaturated fatty acid or a salt thereof, preferably an omega-9 fatty acid or a salt thereof, more preferably a monounsaturated omega-9 fatty acid or a salt thereof, more preferably oleic acid or sodium oleate.

The total amount of the co-surfactant is preferably in the range of from 0.01 wt. % to 1 wt. %, more preferably in the range of from 0.02 wt. % to 0.5 wt. %, more preferably in the range of from 0.02 wt. % to 0.20 wt. % based on the total weight of the emulsion.

The Co-Solvent

The emulsion according to the disclosure may further comprise a pharmaceutically acceptable co-solvent.

The term co-solvent refers to molecules that may increase the stability of the emulsion. In addition to making the environment more hydrophobic by reducing the dielectric constant of water, co-solvents increase the amount of molecularly dispersed emulsifier and/or co-surfactant in the aqueous phase. Availability of free surfactant aids in the solubilization of hydrophobic molecules by creating pockets of hydrophobic regions within the aqueous phase.

The co-solvent may be selected from the group consisting of ethanol, propylene glycol and polyethylene glycol.

Preferably, the co-solvent is a polyalkylene glycol or an alkylene glycol, preferably polyethylene glycol or polypropylene glycol, more preferably polyethylene glycol (PEG).

The PEG preferably has a mean molecular weight in the range of from 100 to 20000 Da, more preferably in the range of from 200 to 1000 Da, more preferably in the range of from 300 to 600 Da, most preferably around 400 Da.

Preferably, the co-solvent is selected from the group consisting of PEG 200, PEG 300, PEG 400, PEG 600, PEG, 1000, PEG 1450, PEG 4000, PEG 6000, PEG 8000 and PEG 20000. Most preferably, the co-solvent is PEG 400.

Preferably, the total amount of co-solvents ranges from 0.1 wt % to 2.0 wt. %, more preferably from 0.25 wt. % to 1.75 wt. %, more preferably from 0.50 wt. % to 1.50 wt. %, more preferably from 0.70 wt. % to 1.40 wt. %, more preferably from 0.80 wt. % to 1.30 wt. %, and even more preferably from 0.90 wt. % to 1.20 wt. % based on the total weight of the emulsion.

The Droplet Size

Since the emulsion of the disclosure is an oil-in-water emulsion, the continuos phase is aqueous and comprises oil droplets. These oil droplets are stabilized within the aqueous phase by at least one emulsifier and optionally further additives. The size of the oil droplets depends on the qualitative and quantitative composition of the emulsion and its preparation.

The oil droplets of the emulsion herein preferably have a mean diameter of 150 to 350 nm when measured directly upon sterilization using an LS 13 320 Laser Diffraction Particle Size Analyser (Beckman Coulter) according to USP <729>.

Preparation of the Emulsion

The present disclosure also relates to a method for preparing an emulsion for parenteral administration and to an emulsion obtained or obtainable by said method, wherein the method comprises a) providing an oil phase comprising vitamin A and one or more lipids and optionally at least one pharmaceutically acceptable antioxidant and/or a pharmaceutically acceptable co-surfactant, b) providing an aqueous phase comprising water for injection and optionally a pharmaceutically acceptable tonicity agent and/or an agent for pH adjustment and/or a pharmaceutically acceptable co-surfactant and/or a pharmaceutically acceptable co-solvent, c) forming a pre-emulsion by mixing the oil phase provided in step a) with the aqueous phase provided in step b);

d) forming the emulsion by high-pressure homogenizing the pre-emulsion obtained in step c) and e) sterilizing the emulsion obtained in step d), wherein the at least one pharmaceutically acceptable emulsifier is added either in step a or in step b.

It is to be understood that any of the optional further components of the emulsion may be added in any of the steps a), b), c) or d) or in one or more additional steps.

Step a)

Step a) is preferably carried out by mixing one or more lipids and vitamin A and optionally the at least one antioxidant and/or the co-surfactant. This step is preferably carried out at a temperature of 50 to 65° C., wherein during this step the temperature may be varied or held essentially constant for a maximum 30 minutes until a homogeneous and clear phase is obtained.

It is to be understood that in step a) further additives may be added.

Step b)

Step b) is preferably carried providing water for injection and optionally adding the tonicity agent and/or the co-surfactant.

The aqueous phase is then heated to a temperature of 55 to 80° C., preferably for a time of 1 minute to 1 hour, more preferably from 5 to 30 minutes, more preferably from 5 to 15 minutes.

Preferably, step b) further comprises adjusting the pH to values between 7 and 10, preferably to a pH between 8 and 9, preferably by adding a solution of NaOH.

It is to be understood that in step b) further additives may be added.

In particular, it is to be understood that the at least one pharmaceutically acceptable emulsifier—depending on its nature—may be added either in step a) or in step b).

Step c)

The method further comprises mixing the oil phase provided in step a) with the aqueous phase provided in step b) thereby forming a pre-emulsion. The mixing may be carried out by any method known to those skilled in the art. Preferably, the mixing is carried out using a high shear mixer.

Preferably the oil phase is added to the aqueous phase or vice-versa at a temperature in the range of from 50 to 80° C.

Preferably the oil phase is added to the aqueous phase or vice-versa at a pressure such as under nitrogen pressure, in the range of from 0.20 to 0.80 bar, more preferably from 0.2 to 0.4 bar. During this step the pressure may be varied or held essentially constant.

According to a preferred embodiment, the mixture is stirred for a time in the range of from 1 minute to 1 hour, preferably from 10 to 30 minutes. During this step, the temperature may be varied or held essentially constant.

It is to be understood that further components may also be added after the formation of the pre-emulsion. According to a preferred embodiment, the pH of the pre-emulsion is adjusted to a pH in the range of from 8 to 10, in particular by adding sodium hydroxide, if necessary.

Step d)

The method further comprises the homogenization of the pre-emulsion obtained in step c). This homogenization may be carried out by any suitable method known to those skilled in the art.

Preferably the mixture is homogenized at a temperature in the range of from 40 to 70° C., preferably from 40 to 60° C., more preferably from 50 to 60° C.

Preferably, the pre-emulsion is homogenized at a pressure in the range of from 400 to 600 bar, more preferably from 450 to 550 bar. During this step the pressure may be varied or held essentially constant.

Preferably, the homogenization is carried out using a high pressure homogenizer or a microfluidizer.

Step e)

The method further comprises the sterilization of the emulsion obtained in step d) to ensure its suitability for parenteral administration.

The sterilization may be carried out by any suitable method known to those skilled in the art. In particular, the sterilization is carried out by autoclaving, preferably at a temperature in the range of from 119 to 122° C., more preferably at a temperature around 121° C., preferably for a time in the range of from 1 minute to 30 minutes, preferably of from 10 minutes to 15 minutes.

Route of Administration

The compositions according to the present disclosure are adapted for parenteral administration, i.e. for a route of administration "other than via the gastrointestinal tract". This includes for example the intravenous, intra-arterial, intramuscular, intraperitoneal and subcutaneous administration.

Preferably, the compositions according to the present disclosure are administered intravenously.

The present disclosure includes inter alia the following aspects:

In a first aspect the present disclosure relates to an emulsion for parenteral administration comprising 1000 to 5000, preferably 1500 to 3000 IU vitamin A per ml, being free of polysorbates and polyoxyethylene/polyoxypropylene block copolymers.

In a second aspect the present disclosure relates to an emulsion according to aspect 1, comprising vitamin A in a form other than beta-carotene, preferably in a form other than carotenoid.

In a third aspect the present disclosure relates to an emulsion according to aspect 1, comprising retinyl palmitate.

In a fourth aspect the present disclosure relates to an emulsion according to aspect 2, wherein in the whole amount of vitamin A is provided in form of retinyl palmitate.

In a fifth aspect the present disclosure relates to an emulsion according any of the preceding aspects, wherein vitamin A is the sole vitamin comprised as an active ingredient.

In a sixth aspect the present disclosure relates to an emulsion according to any of the preceding aspects, wherein the oil phase of the emulsion comprises one or more oils selected from the group consisting of soybean oil, olive oil, fish oil, fish oil extract, safflower oil, corn oil, sunflower oil, coconut oil, palm kernel oil, rapeseed oil and medium chain triglycerides (MCT).

In a seventh aspect the present disclosure relates to an emulsion according to any of the preceding aspects, wherein the oil phase comprises one or more oils selected from the group consisting of fish oil, fish oil extract, MCT, soybean oil and olive oil.

In an eighth aspect the present disclosure relates to an emulsion according to any of the preceding aspects, wherein the oil phase of the emulsion comprises fish oil, fish oil, olive oil, soybean oil and MCT.

In a ninth aspect the present disclosure relates to an emulsion according to any of the preceding aspects, comprising a pharmaceutically acceptable tonicity agent, preferably glycerol.

In a tenth aspect the present disclosure relates to an emulsion according to any of the preceding aspects, comprising at least one co-solvent, preferably polyethylene glycol.

In an eleventh aspect the present disclosure relates to an emulsion according to any of the preceding aspects, comprising an agent for pH adjustment, preferably NaOH.

In a twelfth aspect the present disclosure relates to an emulsion according to any of the preceding aspects, comprising at least one pharmaceutically acceptable emulsifier, preferably lecithin.

In a thirteenth aspect the present disclosure relates to an emulsion according to any of the preceding aspects, comprising a pharmaceutically acceptable co-surfactant, preferably an omega-9 fatty acid or a pharmaceutically acceptable salt thereof, more preferably oleic acid or sodium oleate.

In a fourteenth aspect the present disclosure relates to an emulsion according to any of the preceding aspects, comprising at least one pharmaceutically acceptable antioxidant, preferably selected from the group consisting of alpha-tocopherol, beta-tocopherol, gamma-tocopherol, ascorbic acid, ascorbic acid palmitate, an antioxidant obtained or obtainable from rosemary, rosemary extract and mixtures thereof.

In a fifteenth aspect the present disclosure relates to an emulsion according to any of the preceding aspects, wherein the emulsion is an oil-in-water emulsion and wherein the mean diameter of the oil droplets is between 150 and 350 nm.

In a sixteenth aspect the present disclosure relates to an emulsion according to any of the preceding aspects for use in the treatment or prevention of a vitamin A deficiency, preferably in preterm infants, more preferably in very low birth weight infants, most preferably in extremely low birth weight infants.

In a seventeenth aspect the present disclosure relates to the use of an emulsion according to any of the aspects 1 to 15 for the treatment or prevention of a vitamin A deficiency, preferably in preterm infants, more preferably in very low birth weight infants, most preferably in extremely low birth weight infants.

In an eighteenth aspect the present disclosure relates to the use of an emulsion according to any of the aspects 1 to 15 for supplementing polyunsaturated fatty acids.

In a nineteenth aspect the present disclosure relates to a method for manufacturing the emulsion according to any of the aspects 1 to 15, comprising
a) providing an oil phase comprising one or more oils according to any of the aspects 5 to 7, vitamin A and optionally at least one pharmaceutically acceptable antioxidant and/or a pharmaceutically acceptable co-surfactant;
b) providing an aqueous phase comprising water for injection and optionally a pharmaceutically acceptable tonicity agent and/or an agent for pH adjustment and/or a pharmaceutically acceptable co-surfactant and/or a pharmaceutically acceptable co-solvent;
c) forming a pre-emulsion by mixing the oil phase provided in step a) with the aqueous phase provided in step b);
d) forming the emulsion by high-pressure homogenizing the pre-emulsion obtained in step c) and
e) sterilizing the emulsion obtained in step d), wherein the at least one pharmaceutically acceptable emulsifier is added either in step a or in step b.

Embodiments

1) Emulsion for parenteral administration comprising 1000 to 5000, preferably 1500 to 3000 IU vitamin A per ml, being free of polysorbates and polyoxyethylene/polyoxypropylene block copolymers.
2) Emulsion according to embodiment 1, comprising vitamin A in a form other than beta-carotene, preferably in a form other than carotenoid.
3) Emulsion according to embodiment 1 or 2, comprising retinyl palmitate.
4) Emulsion according to any of the preceding embodiments, wherein the whole amount of vitamin A is provided in form of retinyl palmitate.
5) Emulsion according to any of the preceding embodiments, wherein vitamin A is the sole vitamin comprised as an active ingredient.
6) Emulsion according to any of the preceding embodiments, wherein the oil phase of the emulsion comprises one or more oils selected from the group consisting of soybean oil, olive oil, fish oil, fish oil extract, safflower oil, corn oil, sunflower oil, coconut oil, palm kernel oil, rapeseed oil and medium chain triglycerides (MCT).
7) Emulsion according to any of the preceding embodiments, wherein the oil phase of the emulsion comprises one or more oils selected from the group consisting of fish oil, fish oil extract, olive oil, soybean oil and MCT.
8) Emulsion according to any of the preceding embodiments, wherein the oil phase of the emulsion comprises fish oil, olive oil, soybean oil and MCT.
9) Emulsion according to any of the preceding embodiments, comprising a pharmaceutically acceptable tonicity agent, preferably glycerol.
10) Emulsion according to any of the preceding embodiments, comprising at least one co-solvent, preferably polyethylene glycol.
11) Emulsion according to any of the preceding embodiments comprising an agent for pH adjustment, preferably NaOH.
12) Emulsion according to any of the preceding embodiments comprising at least one pharmaceutically acceptable emulsifier, preferably lecithin.
13) Emulsion according to any of the preceding embodiments comprising a pharmaceutically acceptable co-surfactant, preferably an omega-9 fatty acid or a pharmaceutically acceptable salt thereof, more preferably oleic acid or sodium oleate.
14) Emulsion according to any of the preceding embodiments, comprising at least one pharmaceutically acceptable antioxidant, preferably selected from the group consisting of alpha-tocopherol, beta-tocopherol, gamma-tocopherol, ascorbic acid, ascorbic acid palmitate, an antioxidant obtained or obtainable from rosemary, rosemary extract and mixtures thereof.
15) Emulsion according to any of the preceding embodiments, wherein the emulsion is an oil-in-water emulsion and wherein the mean diameter of the oil droplets is between 150 and 350 nm.
16) Emulsion according to any of embodiments 1 to 15 for use in the treatment or prevention of a vitamin A deficiency, preferably in preterm infants, more preferably in very low birth weight infants, most preferably in extremely low birth weight infants.

17) Use of the emulsion according to any of embodiments 1 to 15 for the treatment or prevention of a vitamin A deficiency, preferably in preterm infants, more preferably in very low birth weight infants, most preferably in extremely low birth weight infants.
18) Emulsion according to any of embodiments 1 to 15 for use in the treatment or prevention of a deficiency in polyunsaturated fatty acids.
19) Use of the emulsion according to any of embodiments 1 to 15 for the treatment or prevention of a deficiency in polyunsaturated fatty acids.
20) Use of the emulsion according to any of embodiments 1 to 15 for supplementing polyunsaturated fatty acids.
21) Method for the preparation of an emulsion according to any of embodiments 1 to 15 comprising
   a) providing an oil phase comprising one or more oils according to embodiment 6 to 8, vitamin A and optionally at least one pharmaceutically acceptable antioxidant and/or a pharmaceutically acceptable co-surfactant,
   b) providing an aqueous phase comprising water for injection and optionally a pharmaceutically acceptable tonicity agent and/or an agent for pH-adjustment and/or a pharmaceutically acceptable co-solvent,
   c) forming a pre-emulsion by mixing the oil phase obtained in step a) with the aqueous phase obtained in step b),
   d) forming an emulsion by high pressure homogenizing the pre-emulsion obtained in step c,
   e) sterilizing the emulsion obtained in step d),
wherein the at least one pharmaceutically acceptable emulsifier is added either in step a or in step b.

EXAMPLES—MONO VITAMIN PREPARATIONS ACCORDING TO THE PRESENT DISCLOSURE

Examples 1 and 2

The emulsions were prepared from the ingredients listed in table 1.

The oil phases were prepared by mixing soybean oil, medium chain triglycerides, olive oil, fish oil, retinyl palmitate and alpha-tocopherol. The mixture was heated to 65° C.

The aqueous phase was prepared by mixing water, glycerol and sodium oleate. The mixture was heated to 70° C., and then egg lecithin was added.

The pre-emulsion was formed by adding the oil phase to the aqueous phase under continuous agitation using a high shear mixer (Ultra Turrax T50) at a temperature of 68° C.

The emulsion was formed by passing the pre-emulsion six times through a Niro Soavi TwinPanda 600 homogenizer at 500 bar at a temperature of 50° C.

The pH was adjusted to 8.0 to 9.0.

TABLE 1

| Ingredient | Amount [g] | |
|---|---|---|
| | Example 1 | Example 2 |
| Soybean oil (oil phase) | 3 | |
| Medium chain triglycerides (oil phase) | 3 | |
| Olive oil (oil phase) | 2.5 | |
| Fish oil (oil phase) | 1.5 | |
| Retinyl palmitate (active ingredient) | 0.082 | 0.165 |
| Egg lecithin (emulsifier) | 1.2 | |
| Alpha-tocopherol (antioxidant) | 0.02 | |

TABLE 1-continued

| Ingredient | Amount [g] | |
|---|---|---|
| | Example 1 | Example 2 |
| Sodium oleate (co surfactant) | 0.03 | |
| Glycerol (tonicity agent) | 2.25 | |
| NaOH (1M) (pH adjustment) | to adjust pH to 8.0-9.0 | |
| Water for injection (aqueous phase) | ad 100 | |

Finally the emulsion was autoclaved at 121° C. for 15 minutes.

The oil droplets of the emulsion according to example 1 had a mean diameter of 172 nm when measured directly upon sterilization. The oil droplets of the emulsion according to example 2 had a mean diameter of 207 nm when measured directly upon sterilization using an LS 13 320 Laser Diffraction Particle Size Analyser (Beckman Coulter) according to USP <729>.

Stability data for both emulsions are shown in table 2.

TABLE 2

| Storage time [w] | Storage T [° C.] | pH | | Mean droplet diameter [nm] | | $PFAT_5$ | |
|---|---|---|---|---|---|---|---|
| | | 1 | 2 | 1 | 2 | 1 | 2 |
| 0 | — | 8.62 | 8.51 | 172 | 207 | 0.017 | 0.036 |
| 1 | 25 | 8.59 | 8.53 | 170 | 214 | 0.011 | 0.018 |
| | 40 | 8.48 | 8.29 | 169 | 213 | 0.013 | 0.023 |
| 2 | 25 | 8.60 | 8.49 | 179 | 232 | 0.005 | 0.014 |
| | 40 | 8.28 | 8.09 | 178 | 308 | 0.004 | 0.024 |

As can be seen in table 2, all PFAT5 values are below 0.05. Thus, both emulsions are stable for at least 2 weeks upon storage at 25 and 40° C.

The invention claimed is:

1. An emulsion for parenteral administration comprising 1000 to 5000 IU vitamin A per ml, being free of polysorbates and polyoxyethylene/polyoxypropylene block copolymers,
   wherein the vitamin A is the sole vitamin comprised as an active ingredient; and
   wherein said vitamin A is in a form other than carotenoid.

2. The emulsion according to claim 1 comprising retinyl palmitate.

3. The emulsion according to claim, wherein the whole amount of the vitamin A is provided in the form of retinyl palmitate.

4. The emulsion according to claim 1, wherein an oil phase of the emulsion comprises one or more oils selected from the group consisting of soybean oil, olive oil, fish oil, fish oil extract, safflower oil, corn oil, sunflower oil, coconut oil, palm kernel oil, rapeseed oil and medium chain triglycerides (MCT).

5. The emulsion according to claim 1, wherein an oil phase of the emulsion comprises fish oil, olive oil, soybean oil and MCT.

6. The emulsion according to claim 1, comprising a pharmaceutically acceptable tonicity agent.

7. The emulsion according to claim 1, comprising at least one co-solvent.

8. The emulsion according to claim 1, comprising an agent for pH adjustment.

9. The emulsion according to claim 1, comprising at least one pharmaceutically acceptable emulsifier.

10. The emulsion according to claim 1, comprising a pharmaceutically acceptable co-surfactant.

11. The emulsion according to claim 1, wherein the emulsion comprises at least one pharmaceutically acceptable antioxidant selected from the group consisting of alpha-tocopherol, beta-tocopherol, gamma-tocopherol, ascorbic acid, ascorbic acid palmitate, an antioxidant obtained or obtainable from rosemary, rosemary extract and mixtures thereof.

12. The emulsion according to claim 1, wherein the emulsion is an oil-in-water emulsion and wherein a mean diameter of the oil droplets is between 150 and 350 nm.

13. The emulsion according to claim 1, for use in the treatment or prevention of a vitamin A deficiency in one or more of: preterm infants, or low birth weight infants.

14. A method for the preparation of an emulsion, comprising:
   a) providing an oil phase comprising one or more oils selected from the group consisting of soybean oil, olive oil, fish oil, fish oil extract, safflower oil, corn oil, sunflower oil, coconut oil, palm kernel oil, rapeseed oil and medium chain triglycerides (MCT); vitamin A; and optionally a pharmaceutically acceptable co-surfactant,
   b) providing an aqueous phase comprising one or more of: water for injection, a pharmaceutically acceptable tonicity agent, an agent for pH-adjustment, or a pharmaceutically acceptable co-solvent,
   c) forming a pre-emulsion by mixing the oil phase obtained in step a) with the aqueous phase obtained in step b),
   d) forming an emulsion by high pressure homogenizing the pre-emulsion obtained in step c, and
   e) sterilizing the emulsion obtained in step d),
   wherein at least one pharmaceutically acceptable emulsifier is added either in step a or in step b;
   wherein said emulsion is an emulsion for parenteral administration comprising 1000 to 5000 IU vitamin A per ml, being free of polysorbates and polyoxyethylene/polyoxypropylene block copolymers,
   wherein the vitamin A is the sole vitamin comprised as an active ingredient; and
   wherein said vitamin A is in a form other than carotenoid.

15. The emulsion according to claim 1, wherein the vitamin A comprises 1500 to 3000 IU vitamin A per ml.

16. The emulsion according to claim 6, wherein the pharmaceutically acceptable tonicity agent comprises glycerol.

17. The emulsion according to claim 7, wherein the at least one co-solvent comprises polyethylene glycol.

18. The emulsion according to claim 8, the agent for pH adjustment comprises NaOH.

19. The emulsion according to claim 9, wherein the at least one pharmaceutically acceptable emulsifier comprises lecithin.

20. The emulsion according to claim 10, wherein the pharmaceutically acceptable co-surfactant comprises one or more of: an omega-9 fatty acid, or a pharmaceutically acceptable salt thereof.

* * * * *